United States Patent [19]

Wall

[11] 4,149,021
[45] Apr. 10, 1979

[54] ESTER HYDROGENATION USING COBALT, ZINC AND COPPER OXIDE CATALYST

[75] Inventor: Robert G. Wall, Pinole, Calif.

[73] Assignee: Chevron Research Company, San Francisco, Calif.

[21] Appl. No.: 899,759

[22] Filed: Apr. 24, 1978

Related U.S. Application Data

[60] Division of Ser. No. 790,366, Apr. 25, 1977, Pat. No. 4,113,662, which is a continuation-in-part of Ser. No. 711,909, Aug. 5, 1976, abandoned, which is a continuation-in-part of Ser. No. 578,799, May 19, 1975, abandoned.

[51] Int. Cl.$^2$ .............................................. C07C 29/00
[52] U.S. Cl. ..................................... 568/864; 568/885
[58] Field of Search ............................... 568/864, 885

[56] References Cited

U.S. PATENT DOCUMENTS

| | | | |
|---|---|---|---|
| 1,949,109 | 2/1934 | Pier et al. | 252/473 |
| 2,023,383 | 12/1935 | Schrauth et al. | 568/885 |
| 2,093,159 | 9/1937 | Schmidt | 568/885 |
| 2,110,483 | 3/1938 | Guyer | 568/885 |
| 2,121,367 | 6/1938 | Schiller | 568/885 |
| 2,285,448 | 6/1942 | Loder | 568/864 |

FOREIGN PATENT DOCUMENTS

| | | |
|---|---|---|
| 1146483 | 4/1963 | Fed. Rep. of Germany. |
| 417582 | 7/1933 | United Kingdom. |
| 457358 | 11/1936 | United Kingdom. |
| 484995 | 5/1938 | United Kingdom. |

*Primary Examiner*—Joseph E. Evans
*Attorney, Agent, or Firm*—D. A. Newell; John Stoner, Jr.; A. T. Bertolli

[57] ABSTRACT

A process for hydrogenation of esters to alcohols which comprises contacting the ester with hydrogen and a catalyst comprising cobalt, zinc and copper under catalytic hydrogenation conditions including a temperature between 150° and 450° C. and a pressure of 500–10,000 psig.

10 Claims, No Drawings

ESTER HYDROGENATION USING COBALT, ZINC AND COPPER OXIDE CATALYST

CROSS-REFERENCE TO RELATED APPLICATION

This application is a division of U.S. application Ser. No. 790,366, filed Apr. 25, 1977, now U.S. Pat. No. 4,113,662, which in turn is a continuation-in-part of U.S. application Ser. No. 711,909, filed Aug. 5, 1976, now abandoned, which in turn is a continuation-in-part of U.S. application Ser. No. 578,799, filed May 19, 1975, now abandoned.

BACKGROUND OF THE INVENTION

The present invention relates to the hydrogenation of esters to alchols using a solid hydrogenation catalyst.

The hydrogenation of esters to alcohols is well known. See, for example, U.S. Pat. No. 1,605,093 disclosing the following ester hydrogenation reaction:

$$R \cdot COO \cdot R' + 2H_2 = R \cdot CH_2OH + R' \cdot OH$$

According to U.S. Pat. No. 1,605,093, a copper catalyst is used in the ester hydrogenation.

It is frequently stated that the best method of converting an acid to the corresponding alcohol usually involves proceeding through the ester. Esters are normally obtained from acids in nearly quantitative yields, and the esters can be reduced to alcohols, usually with considerably higher yields than in reducing the corresponding acid to the alcohol. Esters have been reduced using various means such as lithium aluminum hydride, sodium plus an alcohol, or a solid hydrogenation catalyst. These methods are indicated in general by the equations below:

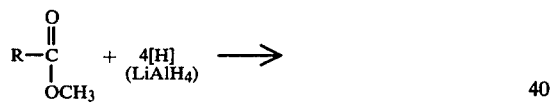

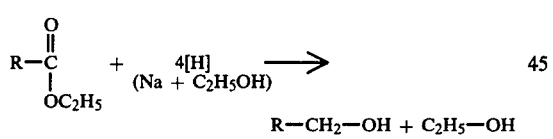

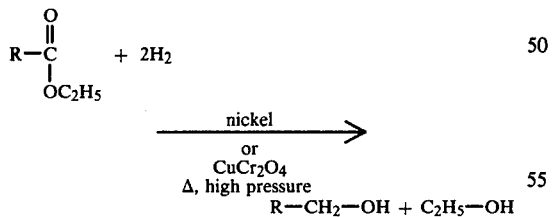

Besides copper chromite as an ester hydrogenation catalyst, as indicated in the last equation above, other hydrogenation catalysts, such as the copper chromite/barium catalyst in U.S. Pat. No. 2,091,800 to Homer Adkins et al, have been disclosed.

U.S. Pat. No. 2,093,159 discloses a

"process for the catalytic hydrogenation of esters of aliphatic alkylmonocarboxylic acids, which comprises passing the said esters together with hydrogen while heating to a temperature of the range from 200° to 400° C. over a hydrogenating catalyst essentially comprising cobalt in combination with an activating substance, selected from the class consisting of oxides of metals giving acids with oxygen and compounds of alkali, alkaline earth and rare earth metals with metal acids until substantial quantities of alcohols corresponding to the said alkylmonocarboxylic acid radicals are formed."

According to the disclosure of U.S. Pat. No. 2,093,159,

"Suitable catalytic substances are for example copper, nickel, silver, zinc, cadmium, lead or cobalt or mixtures thereof and they may be prepared from their salts, oxides or other compounds prior to or after an incorporation with activating substances. The activating substances may be chosen from compounds of the metals giving acids with oxygen, such as chromium, molybdenum, tungsten, uranium, manganese, vanadium or titanium or mixtures thereof as well as from compounds of the alkali, alkali earth or rare earth metals."

U.S. Pat. No. 2,109,844 teaches away from the use of cobalt-containing catalysts in converting esters to alcohols. At page 5 U.S. Pat. No. 2,109,844 states:

"... if the hydrogenation of a fatty glyceride is to be operated for the production of alcohols and esters to the substantial exclusion of hydrocarbons it is preferable to select as the catalyst a composition comprising a member of the group of nonferrous hydrogenating metals such as copper, tin, silver, cadmium, zinc, lead, their oxides and chromites, and oxides of manganese and magnesium. Especially good results are obtained with finely divided copper oxide, either wholly or partially reduced and preferably supported upon an inert surface-extending material such as kieselguhr, or promoted by such oxide promoters as manganese oxide, zinc oxide, magnesium oxide, or chromium oxide. The above mentioned mild-acting catalysts may be termed the alcohol-forming catalysts to distinguish them from the more energetic ferrous metal groups. Elementary nickel, cobalt, and iron when suitably supported on kieselguhr may be used to effect the reduction of fatty glycerides with hydrogen, but in these cases the product contains besides alcohols and waxes a preponderance of hydrocarbons, and this disadvantage in most cases will prove so serious as to preclude the use of these catalysts unless the hydrocarbons themselves are the desired end products."

Other patents which disclose catalysts for hydrogenation of esters and carboxylic acids include U.S. Pat. Nos. 2,110,843; 2,118,007; 2,121,367; 2,782,243; 3,173,959 (copper-zinc chromite catalyst for ester reduction); 3,267,157 (activated copper chromite catalyst for acid and ester hydrogenation).

U.S. Pat. No. 2,285,448 discloses hydrogenation of glycolic acid and its esters to obtain ethylene glycol. According to U.S. Pat. No. 2,285,448, a copper-magnesium catalyst is preferred. At column 2, line 46 of U.S. Pat. No. 2,285,448 it is stated that:

"In place of magnesium oxide, other metal oxides which promote the activity of the copper oxide may be employed such, for example, as an oxide of nickel, iron, cobalt, manganese, chromium, calcium, barium, strontium, potassium, caesium, zinc, cadmium and silver, or mixtures thereof."

SUMMARY OF THE INVENTION

According to the present invention a process is provided for hydrogenation of carboxylic acid esters to alcohols, which process comprises contacting the ester with hydrogen gas and a catalyst comprising cobalt, zinc and copper under catalytic hydrogenation conditions including a temperature between 150° and 450° C. and pressures of 500 to 10,000 psi. This may be either a liquid or vapor phase process, preferably liquid phase.

Among other factors, the present invention is based on my finding that the cobalt-zinc-copper catalyst is a highly effective ester hydrogenation catalyst in terms of activity, selectivity, and stability. The high stability of the catalyst is particularly surprising since catalytically active cupric oxide would be expected to be reduced to inactive copper metal under the hydrogenation conditions. In Organic Reactions, vol. VIII (1954), published by John Wiley & Sons, New York, on page 8 concerning copper chromite Adkins states:

"The catalyst is inactivated if, through excessive temperatures in the preparation or use of the catalyst, the cupric oxide reacts with cupric chromite to give cuprous chromite, $Cu_2Cr_2O_4$, and oxygen. However, the most frequent cause of inactivation of the catalyst is the reduction of the cupric oxide to copper. This is evidenced by a change in the color of the catalyst from black to a copper red. Such a deactivation of the catalyst is favored by the presence of water, acids, or ammonia in the reaction mixture. The reduction and inactivation of the catalyst may be minimized by precipitating barium (or strontium or calcium) chromate along with the basic copper ammonium chromate in the first step in the preparation of the catalyst."

In agreement with Adkins, I frequently find that the less stable catalysts turn "copper red" with use while the more stable catalysts remain gray to black.

According to preferred embodiments of the present invention, the ester feedstock is a polyglycolide $H(C_2H_2O_2)nOH$ derived from glycolic acid, dialkyl oxalate, aliphatic monocarboxylic acid ester, aliphatic dicarboxylic acid diester, or alpha-hydroxy mono-carboxylic aliphatic acid ester. The term aliphatic is used to include alicyclic.

For the aliphatic acid esters, preferably the aliphatic groups are $C_2$ (including acetates) to $C_{30}$ and preferably they are saturated. The aliphatic groups may be both acyclic and cyclic. The other moiety of the ester (alcohol-derived moiety) is preferably a $C_1$ to $C_{20}$ alkyl group or alkyl hydroxy group such as from ethylene glycol. By the term "alcohol-derived moiety" is meant the group attached by ether linkage to the carbonyl group of the ester.

Preferred dialkyl oxalate ester feedstocks are those wherein the alkyl groups are $C_1$ to $C_{20}$, more preferably $C_1$ to $C_4$. Hydrogenation of the dialkyl oxalate yields ethylene glycol and alkyl monools.

Preferred aliphatic carboxylic acid ester feeds are of the formula

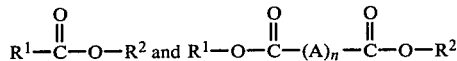

wherein $R^1$ and $R^2$ are $C_1$ to $C_{20}$ alkyl groups, $n=0$ or 1 and A is an alkylene group of 1 to 10 carbon atoms which may be branched chain, and preferably is saturated with hydrogen.

The term "carboxylic acid esters" is used herein in the sense of esters composed of carbon, hydrogen, and oxygen and preferably not containing any halogen, sulfur or nitrogen—that is, at least no halogen, sulfur, or nitrogen or the like in an active form or degradable form such that the ester hydrogenation reaction is substantially prevented.

The most preferred feeds for the process of the present invention are ethylene glycol glycolate, diethylene glycol glycolate, and polyglycolides (typically the polyglycolide feeds are in the form of an alkyl glycolate obtained from the polyglycolide and solvent alcohol).

The ethylene glycol glycolate can be obtained from glycolic acid by reaction of ethylene glycol with glycolic acid or its oligomers under usual esterification conditions. Likewise, the diethylene glycol glycolate can be obtained by reaction of glycolic acid or its oligomers with diethylene glycol. Both the monoglycolates and the bisglycolates of these glycol solvents, i.e., ethylene glycol and diethylene glycol, can be hydrogenated in the present process.

Polyglycolide can be obtained by dehydrating glycolic acid, for example by heating glycolic acid under vacuum and removing water. Preferably the process of the present invention is carried out in the presence of an alcohol solvent for the ester feed so that in the case of the polyglycolide feed the polyglycolide would be in the form of the ester resulting from the reaction of the alcohol solvent with the polyglycolide. Polyglycolide reacts with alcohols to form esters with less formation of water than would be the case in reacting glycolic acid directly with an alcohol. The general reaction for the polyglycolide with an alcohol solvent to form a glycolate is as follows:

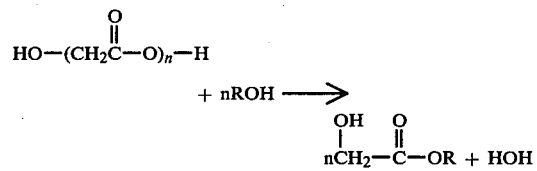

Thus in the case of $n=5$ there would be 5 mols of the glycolate for one mol of water.

Preferred solvents for the ester hydrogenation process of the present invention are $C_1$-$C_{20}$ alkyl alcohols. Ethylene glycol and diethylene glycol are especially preferred solvents. Lower alcohols such as methanol, ethanol, and propanol and butyl alcohols are also advantageous solvents. Preferred amounts of the alcohol solvent are 0.1-10 parts per one part ester feed by weight, more preferably 0.5-3 parts per one part ester feed. Preferably the alcohol solvent is not an unsaturated alcohol nor an aromatic alcohol.

Although the reaction of the present invention has been carried out in mixed liquid-vapor phase, generally it is preferred to carry out the reaction with the ester and the alcohol solvent in the liquid phase. Typically the hydrogen remains in gaseous phase except for dissolved hydrogen.

Suitable pressures are between about 500 and 10,000 psig, preferably between 1,000 and 5,000 psig. Preferred hydrogenation reaction temperatures are 100° to 350° C., more preferably 180°-250° C. Suitable hydrogen to ester molar ratios are between 1.1/1 and 100/1, and preferably between 1.5/1 and 10/1. Suitable liquid hourly space velocities for the ester feed over the catalyst are between 0.1 and 100 and preferably are between 0.5 and 10.

The cobalt, zinc and copper components of the catalyst can be present in the catalyst in elemental form or in compound form, such as in the oxide form. In the fresh catalyst the components are present in compound form as in the oxide, hydroxide, carbonate or complex salt. Under hydrogenation conditions or after use, the components may be partly or largely in elemental form. For example, cobalt may be reduced to the elemental form while copper and zinc remain mostly in compound form, particularly as the oxide. Preferred amounts of the cobalt, zinc and copper for the catalyst are between 10 and 50 weight percent cobalt, 10 and 50 weight percent zinc, and 1 and 50 weight percent copper, and particularly preferred amounts are between 15 and 40 weight percent cobalt, 15 and 40 weight percent zinc, and 1 and 40 weight percent copper.

The catalyst can be used in unsupported form or in supported form. When used in supported form, the weight percent of the support as, for example, alumina, silica, charcoal, or other porous support, can be between about 50 and 98 weight percent of the catalyst with the cobalt, zinc and copper components being disposed on the support in weight amounts as previously given, correspondingly reduced in view of the weight percent of the catalyst support.

The catalyst used in the present invention must contain cobalt, zinc and copper but in addition to support material for the catalyst other materials may be included in the catalyst so long as they do not block the effectiveness of the catalyst. As shown by the examples hereinbelow, nickel may be added to the cobalt-zinc-copper catalyst.

EXAMPLE I

Typically the catalytic solids are prepared by precipitation from aqueous solution using an aqueous solution of base as the precipitating agent. The precipitated solids are isolated, washed, dried and calcined before use. The following is a typical preparation of a coprecipitated cobalt-zinc-copper oxide catalyst.

A solution of 30 g (0.1 mole) $Co(NO_3)_2 \cdot 6H_2O$, 30 g (0.1 mole) $Zn(NO_3)_2 \cdot 6H_2O$ and 24 g (0.1 mole) $Cu(NO_3)_2 \cdot 3H_2O$ in 500 ml of distilled water is added dropwise with stirring to a solution of 40 g (0.42 mole) $(NH_4)_2CO_3$ in 400 ml of distilled water. The precipitate is recovered by filtration and washed four times with 500 ml portions of distilled water. The wet solid is dried overnight in a vacuum oven (typically 80° C., 200-500 mm Hg) and calcined in air for 4 hours at 100° C., 4 hours at 200° C. and for 16-20 hours at 500° C. The yield of catalyst powder is 20-25 g. A fresh catalyst prepared in this way had a surface area of 55 m²/g.

The separately precipitated metal salts and other combinations of the metal oxides were also prepared in this way.

EXAMPLE II

An effective catalyst can also be prepared in the following manner. A solution of 22 g (0.1 mole) $Zn(OAc)_2 \cdot 2H_2O$, 25 g (0.1 mole) $Co(OAc)_2 \cdot 4H_2O$ and 20 g (0.1 mole) $Cu(OAc)_2 \cdot H_2O$ in 500 ml of distilled water is stirred while a solution of 40 g (0.42 mole) $(NH_4)_2CO_3$ in 400 ml of distilled water is added. The precipitate is isolated by filtration, washed with distilled water and dried overnight in a vacuum oven. The dried catalyst is calcined 2 hours at 100° C., 2 hours at 200° C. and for 16-20 hours at 250° C. The yield is 25-30 g of catalyst powder. A fresh catalyst prepared in this way had a surface area of 139 m²/g.

Examples I and II illustrate typical methods used to prepare the hydrogenation catalysts effective in the invention. In both examples, the catalyst was washed, dried, and calcined prior to use. It has been found that the calcination step is particularly important when hydrogenating concentrated solutions of glycol glycolate. Significant amounts of metal, especially zinc, are lost during the hydrogenation reaction unless the final calcination is carried out at temperatures above 300° C. This can lead to catalyst deterioration in long-term hydrogenation runs. Accordingly, in a preferred method of preparation, the dried catalyst is calcined by heating at a temperature of from about 200° C. to about 300° C. until carbonates and hydrates are substantially completely decomposed and then heated at a temperature of from about 400° C. to about 500° C. for 0.5 to 16 hours or more. In a preferred method, the catalyst is calcined by heating at about 250° C. for about 2 hours and then at about 450° C. for about 16 hours. The following Table illustrates the relative stability of catalysts calcined above 300° C. compared to catalysts calcined at 300° C. and 250° C. in the hydrogenation of glycol glycolate solutions. As can be seen, the hydrogenated glycol product obtained using the three low temperature catalysts contained significant amounts of zinc, indicating catalyst decomposition.

| Calcination, ° C. | Zinc ppm in Product |
| --- | --- |
| 300 | 42 |
| 250 | 16 |
| 250 | 20 |
| 450 | 0.6 |
| 450 | 1.0 |
| 450 | 0 |

EXAMPLE III

For the hydrogenations, polyglycolide was prepared from commercially available aqueous glycolic acid (70% solution) by vacuum distillation removal of most of the water. The equivalent weight of the polyglycolide was determined by saponification and titration. Hydrogenations were carried out on mixtures of 7 g polyglycolide and 60 g of methanol in a rocking autoclave. Product analyses were by vapor phase chromatography using an internal standard.

Several commercially available copper chromite ester hydrogenation catalysts were tested. The following results were obtained using 5 g of catalyst at 250° C. and 3000-3500 psig for 8 hours. The best of these,

| Copper Chromite Catalyst | Conversion to Ethylene Glycol |
| --- | --- |
| Harshaw Cu1110-P | 27% |
| Calsicat* 102 | 25% |
| Harshaw Cu0401-P | 51% |
| Calsicat* 101 | 81% |
| Calsicat* 104 | 90% |

*Calsicat is a Division of the Mallinckrodt Chemical Works.

Calsicat 104, was compared with the metal oxides prepared according to Example I. These hydrogenations were carried out for 1 hour at 250° C. on 7 g polyglycolide in 60 g of methanol. These results demonstrate that the coprecipitated cobalt-zinc-copper oxide catalyst (I) is superior to the commercial copper chromites, the individual oxides, and to the coprecipitated cobalt-zinc oxide for this hydrogenation.

| Catalyst | Wt. of Catalyst | Pressure psig | Conversion to Ethylene Glycol |
|---|---|---|---|
| Calsicat 104 | 5g | 3450 | 79% |
| Co-Zn-Cu Oxides (I) | 5g | 2450 | 82% |
| Co-Zn Oxides | 5g | 2560 | 32% |
| Cu Oxide | 2.5g | 2250 | 42% |
| Zn Oxide | 2.5g | 2650 | 0% |
| Co Oxide | 2.5g | 2650 | 0% |

EXAMPLE IV

Comparisons were also made in a stirred autoclave at 250° C. using 7 g polyglycolide (prepared as in Example III), 60 g ethanol, and 5 g catalyst. These results show that I is superior to the commercial copper chromite and to the coprecipitated cobalt-copper oxides. The coprecipitated copper-zinc oxide is equal to I in this test but further work shows I to be more stable. The results also show that a physical mixture of the separately prepared metal oxides (hereinafter referred to as: I, physical mixture) with the same composition as I is an effective catalyst.

| Catalyst | Pressure | Time | Conversion to Ethylene Glycol |
|---|---|---|---|
| Calsicat 104 | 3550 psig | 2 hrs | 80% |
| I | 2700 psig | 0.5 hr | 90% |
| Co-Cu Oxides | 2800 psig | 1 hr | 42% |
| Cu-Zn Oxides | 3200 psig | 0.5 hr | 90% |
| I, physical mixture | 3100 psig | 0.5 hr | 87% |

EXAMPLE V

Catalyst stability comparisons were carried out by recycling recovered used catalysts with fresh feed. In each cycle 7 g polyglycolide (prepared as in Example III) and 60 g of solvent were used. In each case there was 5 g of fresh catalyst in the first cycle. Hydrogenations were run for 30 min at 250° C. and 2800–3100 psig.

| Catalyst | Solvent | Cycle (s) | Conversion to Ethylene Glycol |
|---|---|---|---|
| I | ethanol | 1–4 | 90% |
| Cu-Zn oxides | ethanol | 1 | 90% |
| Cu-Zn oxides | ethanol | 2 | 82% |
| Cu-Zn oxides | ethanol | 3 | 62% |
| I, (physical mixture) | methanol | 1 | 87% |
| I, (physical mixture) | methanol | 2 | 83% |
| I, (physical mixture) | methanol | 3 | 82% |
| I, (physical mixture) | methanol | 4 | 45% |

Both I and I (physical mixture) show greater stability than the coprecipitated Cu-Zn oxides.

EXAMPLE VI

Coprecipitated cobalt-zinc-copper oxide catalysts with lower levels of copper were prepared according to the procedure of Example I. The following results were obtained in a rocking autoclave using 7 g polyglycolide (prepared as in Example III), 60 g methanol and 5 g catalyst at 250° C. and 2500 psig for 1 hour. These results demonstrate that even very small amounts of copper have a favorable effect on catalyst performance. However, I have found that copper concentrations above about 0.1 g-atom per g atom of cobalt are preferred for the process of the present invention. Preferably about 0.3 to 2.0 g atoms of zinc and 0.1 to 2.0 g-atoms of copper are used in the catalyst per g atom of cobalt.

| Catalyst | Atom Ratio | Conversion to Ethylene Glycol |
|---|---|---|
| Co-Zn oxides | Co/Zn = 1/1 | 32% |
| Co-Zn-Cu oxides | Co/Zn/Cu = 1/1/0.1 | 67% |
| Co-Zn-Cu oxides | Co/Zn/Cu = 1/1/0.2 | 84% |

EXAMPLE VII

In another comparison polyglycolide (prepared as in Example III) was esterified with methanol prior to hydrogenation. In these cases 7 g polyglycolide was reacted with 60 g of methanol for 30 min at 200° C. This procedure converted about 90% of the polyglycolide to methyl glycolate. Catalyst was added and the hydrogenation was carried out at 250° C. and 2700 psig for 30 min. Only 0.5 g of catalyst was used.

| Catalyst | Conversion to Ethylene Glycol |
|---|---|
| Calsicat 104 | 11% |
| I | 63% |
| II (Example II) | 77% |
| Calsicat 101 | 3.2% |
| Harshaw Cu0401P | 2.3% |

Both I and II (coprecipitated Co-Cu-Zn oxides from Example II) are far superior to the commercial catalysts.

EXAMPLE VIII

The above results were obtained using methyl glycolate prepared directly from polyglycolide. These mixtures contain small amounts of impurities such as water and unmethylated glycolates which could affect catalyst performance. Therefore, comparisons were made with distilled 99.6% methyl glycolate. These runs were in a rocking autoclave with 10 g of methylglycolate, 60 g of methanol and only 0.1 g of catalyst at 250° C. and 2800 psig for 2.5 hours.

| Catalyst | Conversion to Ethylene Glycol |
|---|---|
| Calsicat 104 | 30% |
| I | 89% |
| II | 76% |
| II (Co/Zn/Cu = 1/1/2) | 63% |
| II (Co/Zn/Cu = 1/1/0.5) | 58% |
| Cu-Zn oxides | 30% |

With these high substrate to catalyst ratios and pure methyl glycolate the results again show I and II to be superior to a good commercial copper chromite (and to the Cu-Zu oxides prepared according to Example I). Also catalysts prepared according to Example II with Co/Zn/Cu ratios of 1/1/2 and 1/1/0.5 were effective catalysts.

EXAMPLE IX

Ethyl laurate (22.8 g) was hydrogenated in a stirred autoclave for 4 hours at 250° C. and 3000 psig with 60 g ethanol and 5 g of catalyst. Saponification-titration analysis showed 73% conversion with Calsicat 104 and 86% conversion with I. Chromatographic analysis showed the presence of 1-dodecanol.

EXAMPLE X

Diethyloxalate (17.5 g) was hydrogenated in a stirred autoclave for 1 hour at 250° C. and 3400 psig with 60 g of ethanol and 5 g of catalyst. Calsicat 104 converted 58% of the diethyloxalate to ethylene glycol compared to 72% with I.

EXAMPLE XI

Polyglycolide was esterified with diethylene glycol to obtain diethylene glycol glycolate as the feed to the ester hydrogenation step. The saponification equivalent was 516 g or 32% ester concentration calculated as diethylene glycol glycolate. An 80 g portion of this solution was hydrogenated in a rocking autoclave at 225° C./1500 psig for 6 hours using 0.5 g of catalyst prepared according to Example I. The conversion to ethylene glycol was 77%. The ethylene glycol productivity was 2.5 g per g of catalyst each hour.

EXAMPLE XII

A solution of 50% diethylene glycol glycolate in diethylene glycol was hydrogenated as in Example XI. The conversion was 57% to ethylene glycol or a productivity of 2.6 g per g of catalyst each hour.

EXAMPLE XIII

Catalysts prepared according to Examples I and II were tabletted with sodium meta silicate binder and broken into 20–28 mesh particles. These particles were used to hydrogenate ethylene glycol glycolate/ethylene glycol and diethylene glycolate/diethylene glycol.

| Catalyst | Feed | Conversion to Ethylene Glycol | Glycol Productivity |
|---|---|---|---|
| I-pellets | diethylene glycol glycolate | 38% | 1.1g/gcat,hr |
| II-pellets | diethylene glycol glycolate | 80% | 2.3g/gcat,hr |
| II-pellets | ethylene glycol glycolate | 39% | 1.3g/gcat,hr |

EXAMPLE XIV

A catalyst prepared as in Example II, except that the metal acetate solution was added to the ammonium carbonate solution, was used to hydrogenate a 52% solution of ethylene glycol glycolate in ethylene glycol in a stirred autoclave at 225° C. and 1500 psig. The rate of glycolate conversion was 0.03 mole per g of catalyst each hour.

EXAMPLE XV

A catalyst was prepared as in Example XIV except that the acetate solution also included 0.01 mole of nickel acetate. The finished catalyst was used to hydrogenate ethylene glycol glycolate as in Example XIV. The rate of glycolate conversion was 0.02 mole per g of catalyst each hour. This demonstrates that including nickel in the catalyst still gives an effective hydrogenation catalyst.

What is claimed is:

1. A process of hydrogenation of carboxylic acid esters to alcohols which comprises contacting the ester with hydrogen gas and a catalyst the metals of which are not fused and consisting essentially of the elemental oxide of cobalt, zinc and copper under catalytic hydrogenation conditions including a temperature between 150° and 450° C. and pressures of 500–10,000 psig.

2. A process in accordance with claim 1 wherein the ester is ethylene glycol glycolate, diethylene glycol glycolate, a polyglycolide, alkyl glycolate, dialkyl oxalate, aliphatic monocarboxlic acid ester, aliphatic di-carboxylic acid ester or alpha-hydroxy mono-carboxylic aliphatic acid ester, wherein the alcohol derived moiety of the ester is a $C_1$ to $C_{10}$ alkyl or alkylhydroxy group and the aliphatic group is $C_2$ to $C_{30}$.

3. A process in accordance with claim 2 wherein the ester is dialkyl oxalate, the alkyl groups are $C_1$ to $C_4$, and the temperature is 200° to 300° C.

4. A process in accordance with claim 1 wherein the ester is an aliphatic carboxylic acid ester of the formula

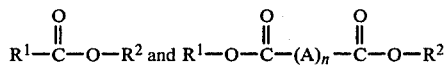

wherein $R^1$ and $R^2$ are $C_1$ to $C_{20}$ alkyl groups, n=0 or 1 and A is an alkylene group of 1 to 10 carbon atoms and the temperature is 200° to 300° C.

5. A process in accordance with claim 1 wherein the ester is ethylene glycol glycolate or diethylene glycol glycolate.

6. A process in accordance with claim 2 wherein the catalyst consists essentially of from 10 to 50 weight percent cobalt, 10 to 50 weight percent zinc, and 1 to 50 weight percent copper.

7. A process in accordance with claim 5 wherein the catalyst consists essentially of from 10 to 50 weight percent cobalt, 10 to 50 weight percent zinc, and 1 to 50 weight percent copper.

8. A process according to claim 5 wherein the catalyst is calcined at a temperature above 300° C.

9. A process in accordance with claim 8 wherein the catalyst is calcined by heating at a temperature from about 200° C. to about 250° C. until carbonates and hydrates are substantially decomposed and heating at a temperature of from about 400° C. to about 500° C. for at least 0.5 hours.

10. A process in accordance with claim 4 wherein the catalyst is calcined by heating at a temperature of about 250° C. for about 2 hours and heating at about 450° C. for about 16 hours.

* * * * *